United States Patent
Paxton-Pierson

(10) Patent No.: US 10,568,900 B1
(45) Date of Patent: Feb. 25, 2020

(54) ANDROGEN EFFECTORS

(71) Applicant: Suzanne Janine Paxton-Pierson, Woodinville, WA (US)

(72) Inventor: Suzanne Janine Paxton-Pierson, Woodinville, WA (US)

( * ) Notice: Subject to any disclaimer, the term of this patent is extended or adjusted under 35 U.S.C. 154(b) by 0 days.

(21) Appl. No.: 14/335,856

(22) Filed: Jul. 18, 2014

Related U.S. Application Data

(60) Provisional application No. 61/802,372, filed on Mar. 15, 2013.

(51) Int. Cl.

| A61K 31/7048 | (2006.01) |
|---|---|
| A61K 31/353 | (2006.01) |
| A61K 31/045 | (2006.01) |
| A61K 31/12 | (2006.01) |
| A61K 31/473 | (2006.01) |
| C07D 407/10 | (2006.01) |
| C07D 311/32 | (2006.01) |
| A61K 31/352 | (2006.01) |
| C07D 493/08 | (2006.01) |

(52) U.S. Cl.
CPC ........ *A61K 31/7048* (2013.01); *A61K 31/045* (2013.01); *A61K 31/12* (2013.01); *A61K 31/352* (2013.01); *A61K 31/353* (2013.01); *A61K 31/473* (2013.01); *C07D 311/32* (2013.01); *C07D 407/10* (2013.01); *C07D 493/08* (2013.01)

(58) Field of Classification Search
CPC . A61K 31/7048; A61K 31/353; A61K 31/045
USPC ............................................. 514/99, 25, 26
See application file for complete search history.

(56) References Cited

U.S. PATENT DOCUMENTS

| 8,524,682 B2 | 9/2013 | Chinnaiyan et al. |
|---|---|---|
| 2007/0036742 A1 | 2/2007 | Roufs et al. |

FOREIGN PATENT DOCUMENTS

| CN | 1239547 A | 12/1999 |
|---|---|---|
| CN | 102985065 A | 3/2013 |
| CN | 103461540 A | 12/2013 |
| DE | 102006062566 A1 | 7/2008 |
| EP | 1430933 A2 | 7/2004 |
| EP | 1595936 B1 | 10/2011 |
| EP | 2371367 A1 | 10/2011 |
| EP | 1448232 B1 | 7/2014 |
| JP | H09227341 * | 9/1997 |
| WO | WO 2004006876 A1 | 1/2004 |
| WO | WO 2004039793 A1 | 5/2004 |
| WO | WO 2008100977 A2 | 8/2008 |
| WO | WO 2009043577 A2 | 4/2009 |
| WO | WO 2011082235 A2 | 7/2011 |
| WO | WO 2012088382 A3 | 11/2012 |

OTHER PUBLICATIONS

Cao et al. Role of P-glycoprotein in the Intestinal Absorption of Glabridin, an Active Flavonoid from the Root of Glycyrrhiza glabra. Drug Metabolism and Disposition 35:539-553, 2007.*
Hu et al. The Cytotoxicity of Methyl Protoneogracillin (NSC-698796) and Gracillin (NSC-698787), Two Steroidal Saponins from the Rhizomes of *Dioscorea collettii* var. hypoglauca, against Human Cancer Cells in vitro. Phytother. Res. 17, 620-626 (2003).*
Armanini et al. Treatment of polycystic ovary syndrome with spironolactone plus licorice. European Journal of Obstetrics & Gynecology and Reproductive Biology 131:61-67, 2007.*
Mattarello et al. Effect of licorice on PTH levels in healthy women. steroids 71:403-408, 2006.*
Angelova et al. Antitumor activity of Bulgarian herb *Tribulus terrestris* L. on human breast cancer cells. J. BioSci. Biotech. 2(1): 25-32, Feb. 2013.*
Somjen et al., "Estrogen-like activity of licorice root constituents: glabridin and glabrene, in vascular tissues in vitro and in vivo" Journal of Steroid Biochemistry & Molecular Biologyvol. 91 pp. 147-155 (Year: 2004).*
Armanini et al., "Reduction of Serum Testosterone in Men by Licorice" New England Journal of Medicine vol. 341 No. 15 p. 1158 (Year: 1999).*
Simons, Vincken, et al, Anal Bioanal Chem (2011) 401:305-313; Agonistic and antagonistic estrogens in licorice root.
Tamir, S. et al, Cancer Res. Oct. 15, 2000;60(20):5704-9; Estrogenic and antiproliferative properties of glabridin from licorice in human breast cancer cells.

* cited by examiner

*Primary Examiner* — Eric Olson

(57) ABSTRACT

The invention discloses novel endocrine treatment phytochemicals which affect androgenic status. The method for treatment of 5-alpha-reductase responsive diseases using four novel 5-alpha-reductase inhibitor compounds; leucoanthocyanidin, glabrene, glabridin, and alpha-terpineol is disclosed. Glabridin does not interfere with normal testosterone to androgen receptor binding.

7 Claims, 1 Drawing Sheet

Figure 1: Glabridin
Figure 2: Leucoanthocyanidin
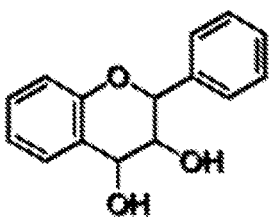
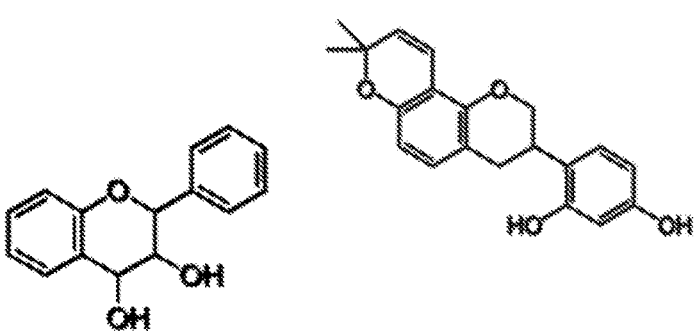
Figure 3: Licochalcone A
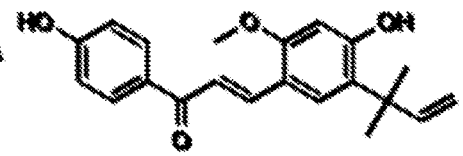
Figure 4: Glabrene
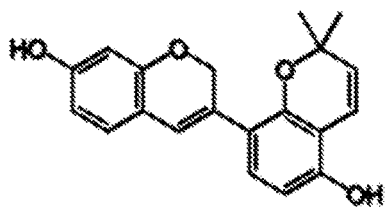
Figure 5: Protogracillin
Protogracillin (25R)-Furost-
5-ene-3β,22α,26-triol 3-O-α-
L-rhamnopyranosyl-(1→2)-
[β-D-glucopyranosyl-
(1→3)]-β-D-
glucopyranoside 26-O-β-D-
glucopyranoside)
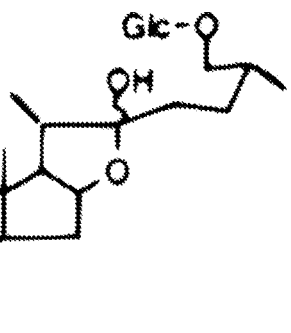
Figure 6: Alpha-terpineol
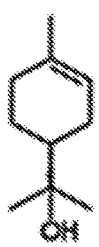

ANDROGEN EFFECTORS

CROSS-REFERENCE TO RELATED APPLICATIONS

This application claims the benefit of provisional patent application No. 61/802,373, filed on Mar. 15, 2013 by the present inventor.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Further Text Filed by EFS-WEB.

STATEMENT REGARDING PRIOR DISCLOSURES BY THE INVENTOR OR A JOINT INVENTOR

Not Applicable

BACKGROUND OF THE INVENTION 5-alpha-reductase converts testosterone into the most potent androgen, dihydrotestosterone (DHT). DHT is a testosterone metabolite via the 5AR enzyme in both males and females. Androgen receptors mediate endocrine processes such as male sexual differentiation of the fetus, muscle growth, anabolism, weight loss, libido, hair loss, and male urine flow. 5 alpha-dihydrotestosterone binds to the androgen receptor to regulate specific gene expression. DHT accumulates in prostate cells with age even as blood testosterone and DHT decline with age. Men suffering from prostate-related urinary symptoms have higher levels of dihydrotestosterone whereas blood testosterone level showed no effect on urinary tract symptoms. DHT affects both male and female alopecia and female hirsutism and poly cystic ovary syndrome (PCOS). PCOS is associated with enhanced androgen and cortisol metabolite excretion and increased 5 alpha-reductase activity and increased adrenal corticosteroid production. Male andropause with its decreased serum testosterone, typically below 300 ng/dL and lower, results in tissues starved of testosterone along with more conversion of existing testosterone to deleterious DHT. The male climacteric entails not only reduced blood testosterone, but an increased ratio of estrogens, FSH, LH and sex-hormone binding globulins.

Estrogens have an important role in the development and progression of benign prostate enlargement. The enzyme aromatase converts testosterone into estradiol. Estrogens can stimulate prostate growth, resulting in hyperplasia of the gland, stimulating proliferation of the stromal cells in the prostate gland that causes many urinary symptoms. Estradiol causes rapid proliferation of prostate stromal cell and anti-estrogen compounds block this undesirable affect. Prostate enlargement sufferers have significantly higher serum estradiol concentrations those without enlargement with 1.78 times higher incidence of urinary tract symptoms. Therefore DHT and estradiol are associated with highest levels of urinary tract symptoms in BPH patients. Estrogenic effects are common with many anti-BPH 5ARI formulations and are undesirable.

5-alpha-reductase inhibition therapies which reduce DHT are prudent. Inhibitors of 5-alpha-reductase are useful for the selective treatment of benign prostate hyperplasia, female PCOS, female hindradenitis ativa, female hirsuitism and male-impaired urine-flow. It is desirable to avoid affecting spermatogenesis, sexual behavior and smooth muscle growth that do not require the conversion of testosterone to 5-alpha-dihydrotestosterone. Testosterone therapy may contribute to increased DHT; therefore treatment of testosterone insufficiency with testosterone may exacerbate BPH. Many anti-DHT therapies are estrogenic.

BPH affects over 60% of men over the age of 50 causing urinary hesitancy, incomplete voiding, terminal dribbling, urgency, frequency and nocturia. Nocturia troubles 80% of men 60-80 years old and 90% of men over 80 years old. Stage I BPH involves obstructive and irritant symptoms. Stage II BPH begins when there is decomposition of the voiding mechanism, leading to residual urine of 100-150 ml and pollakisuria (increased frequency). In Stage III BPH, chronic and complete retention of urine or overflow incontinence causes reduction of renal function and uremia, a disease secondary to renal failure where nitrogenous waste products accumulate in the blood.

BPH-related urinary problems such as incontinence, the inability to control urination, affects some 5% of the population. The condition introduces profound psychological effects, sleep interruption and hygiene issues. Chronic lack of sleep imposes greater risk of other diseases such as cancer, heart attack, depression and inflammatory syndromes. Incontinence can affect both men and women. The standard medical treatments include physiotherapy, diapers, and treatment of both psychological and social problems. Overflow incontinence in males occurs secondary to hormonal imbalances causing narrowing of the urethra from a variety of causes including BPH.

Problems: Preferred anti-DHT treatments possess 5-alpha-reductase inhibition activities such that testosterone conversion to the more active dihydrotestosterone by 5-alpha-reductase is inhibited. Beyond highly potent 5 alpha-reductase inhibiting activity and safety, the preferred compounds would not trigger an estrogenic response at all or to any significant degree. Thus the compounds may simultaneously maintain testosterone receptor efficacy and/or whole-body androgenicity via non-DHT producing analogs, while treating excess DHT conditions in males, e.g. male urine flow impaired and the like and excess DHT conditions in females, e.g. hirsutism, and PCOS. Thus desirable androgenic effects are caused without any increase in either serum testosterone or creation of deleterious DHT. A non-testosterone androgenic receptor agonist which, because it does not increase serum testosterone, cannot be converted to deleterious DHT or lead to higher levels of DHT, would be of benefit to conditions, syndromes and diseases which are worsened by DHT such as pattern alopecia, benign prostatic hypertrophy, urinary obstruction in males, while at the same time testosterone agonism is needed. Accordingly, there is a demand for development of a novel anti-DHT which is completely free of any safety problems, which does not increase testosterone or estrogenic effects. Currently employed medicines as 5-alpha-reductase inhibitors have untoward side effects, either estrogenic, anti-androgenic or others, such as permanent erectile dysfunction with finasteride.

Anticholinergic agents are used as monotherapy or in combination with α1-adrenocepetor inhibitors for patients with storage disorders while phosphodiesterase 5 (PDE5) inhibitors are used for patients with lower urinary tract symptoms and concomitant erectile dysfunction. Examples of problems of current therapies which are primary pharmacological treatments such as alpha 1-adrenoreceptor inhibitors, 5-alpha-reductase inhibitors, anticholinergics and PDE-5 inhibitors.

Antiandrogenicity: *Angelica Tenuissima*, Artocarpin, Beta Sitosterol, Epicatechin, Epigallocatechin, Unsaturated Fatty Acids (GLA, Alpha-Linolenic Acid, Stearic Acid, Linolenic Acid, Linoleic Acid, Palmitoleic Acid, Oleic Acid, Palmitic Acid, Myristoleic Acid and Arachidonic Acid). Medium chain fatty acids such as those found in coconut and the kernel of many palm fruits have also been found to inhibit 5α-reductase. Finasteride, *Perilla sikokiana* (contains linoleic acid and linoleic acid), Pumpkin Seed Lipid Fractions, *Serenoa Repens* (the fruit of saw palmetto contains about 25% fatty acids consisting of capric, caprylic, lauric, palmitic, oleic, linoleic and linoleic acids in the form of fixed oils and campesterol, stigmasterol and beta-sitosterol), *S. Flavescens*.

Estrogenicity: Biochanin-A, Daidzein, Pumpkin Seed Extract (contains lignin phytoestrogens secoisolariciresinol which is intestinally converted to enterodiol, a 5ARI type III), *Serenoa Repens* contains estrogenic 5ARI compounds. (Elghamry 1969), Solasodine, *S. Flavescens* is highly estrogenic, β-sitosterol and other plant phytosterols, Soy genistein and daidzein, *Pygium africanum*.

Other: Flutamide (transaminase elevation, dry skin)

Erectile Dysfunction: cGMP phosphodiesterase inhibitors (PDE5 inhibitors) such as Sildenafil (WO 94/28902) are orally effective agents useful for impotence. 70% of the population over age 50 suffers loss of libido or erectile dysfunctions, often associated with heart or kidney disease. Drugs used include testosterone, VIP, prostaglandin derivatives PGEs and cardiovascular agents such as phenoxybenzamine, phentolamine and papaverine. All of these drugs have untoward side effects or require painful administration such as the intercavernous or intrauerethral injection of papaverine and PGE2. Natural product options widen the approaches. Nitric oxide, cAMP and cGMP messengers, smooth muscle adrenergic receptors, dopaminergic neurotransmitters and PGE-2 or other hormones are pharmacologic targets for impotence and low libido, which is complicated by psychosocial factors.

SUMMARY OF THE INVENTION

Methods: Three assay types were done to determine the usefulness of natural product compounds as 5ARI therapies: Human Androgen Receptor Assay (hAR) in recombinant yeast strain BJ1991 PGKhAR which contains the human androgen receptor (hAR) gene and a built-in color-indicator to androgenicity via an androgen response element (ARE) which is linked to a gene encoding beta-galactosidase, which hydrolyses end terminal B-galactopyranosyl residues on a chlorophenol red-B-D-galactopyranoside releasing colored indicator, chlorophenol red. Thus, test solutions turn further red with androgenicity. Strong agonists appeared deep purple/red while strong antagonists (hAT assay) appeared bright yellow. Weak vs. strong effect was assigned by similarity of color with the control agonist cyproterone acetate (CyAc).

Rat Cytosolic Androgen Receptor Binding Assay was done to test the percent inhibition of testosterone receptor (AR) binding. Licochalcone A at 500 ug/ml has 21% specific binding inhibition. Leucoanthocyanidin at 500 ug/ml had 28% specific binding inhibition. Glabridin at 500 ug/ml has 0% specific binding inhibition (non-antiandrogenic). *Serrenoa* extract (500 ug/ml) showed a 21% specific binding inhibition for testosterone. Leucoanthocyanidin at 500 ug/ml showed a 28% specific binding inhibition for testosterone.

BRIEF DESCRIPTION OF THE SEVERAL VIEWS OF THE DRAWING(S)

The drawings include that of the molecular structures of:
FIG. 1: glabridin,
FIG. 2: leucoanthocyanidin,
FIG. 3: licochalcone A,
FIG. 4: glabrene
FIG. 5: protogracillin
FIG. 6: alpha-terpineol

DETAILED DESCRIPTION OF THE INVENTION

Results and Conclusions: Results for the three assays are presented in the following tables. All samples may be considered inactive in both the hAR and the androgen receptor binding assays. However #1, #4, #5 and #6 were observed to interfere with the activity of 5-alpha-reductase. The IC50 of the positive control compound, finasteride, was approximately 0.07 micrograms/ml.

| Human Androgen Receptor (hAR) assay in recombinant yeast | | | |
|---|---|---|---|
| Name | Concentration Tested (μg/ml) | *hAG (agonist) | *hAT (antagonist) |
| #9 Protogracillin | 100 μg/ml | Active (2) | Inactive |
| #1 Glabrene | 25 μg/ml | Inactive | Inactive |
| #4 Glabridin | 5 μg/ml | Inactive | Inactive |
| #5 Licochalcone A | 5 μg/ml | Inactive | Inactive |
| #6 Leucoanthocyanidin | 500 μg/ml | Clear | Clear |
| Serrenoa Extract | 25 μg/ml | Inactive | Inactive |
| Cyproterone acetate | 0.25 μg/ml | Active (1) | — | hAG agonist component of integrated hAR assay
hAT: antagonist component of integrated hAR assay
*Tested at 100 μg/ml or at the highest concentration permitted by solubility
*Clear* indicates toxicity. In these cases lower doses were tested. Clear means substance killed the yeast, antimicrobial activity. Inactive means no agonist or antagonist activity.

The Androgen Receptor Binding Assay in rat prostatic cytosol as a source of androgen receptors identifies chemicals that have the potential to interact with the androgen receptor (AR) in vitro. Cytosol was incubated with radiolabeled testosterone alone, or in the presence of unlabeled testosterone for the determination of nonspecific binding. The biological action of androgens is mediated through their interaction with the AR; androgens have no hormonal activity in the absence of a functional AR. Due to a high degree of DNA sequence conservation, substances that bind the AR from rats are presumed to be capable of binding the AR in humans. (Kelce, 1998; Betney, 2003). This screening assay measures the receptor-binding affinity of chemicals by evaluating their ability to displace a bound reference androgen, showing the degree of competition for normal androgen binding and activity, either acting as an agonist or antagonist (which is not discerned by the assay).

Specific binding was determined by subtracting values for bound radiolabeled testosterone in the presence of excess unlabeled ligand (nonspecific binding) from values for total binding in the absence of radioinert testosterone.

$$\text{\% Inhibition of specific binding} = 1 - \frac{\text{Specific binding}\{[3H]\text{Test.}+\text{sample}\}}{\text{Specific binding}\{[3H]\text{Test.}\}}$$

Specific binding of the radiolabel in the presence of radioinert testosterone (used as a positive control) or inhibiting compounds was expressed as a percentage of the specific binding of the radiolabel alone Receptor Binding Assay (Rat Prostatic Cytosol)

| Name | Concentration Tested (µg/ml) | *Specific Binding % Inhibition |
|---|---|---|
| #9 Protogracillin | 500 | 0 |
| #1 Glabrene | 125 | 21 |
| #4 Glabridin | 500 | 0 |
| #5 Licochalcone A | 500 | 21 |
| #6 Leucoanthocyanidin | 500 | 28 |
| Serrenoa Extract | 500 | 21 |
| "Testosterone Control** | IC50 | 0.0375 ug/ml (130 nM) |

Nonspecific binding was consistent at 25-30% of total binding.
*Tested at 500 ug/ml or at the highest concentration permitted by solubility.
% of inhibition of specific binding.

Specific receptor activity of protogracillin, a "xenotestosterone," "xenoandrogen" or "testeronomimetic" better isolates for androgenic activity based on recombinant DNA yeast testing for testosterone-analog agonism, interference with endogenous testosterone, and 5-alpha-reductase inhibitory activity. Out of all compounds tested in this array, only protogracillin showed testosterone agonist activity. In vitro testing showed that protogracillin did not interfere with regular testosterone receptor binding; protogracillin also did not inhibit 5AR.

5-alpha-reductase activity was quantified by the extent of conversion of testosterone to dihydrotestosterone in microsomal homogenized rat livers. Spots corresponding to testosterone and androstenedione (the latter serving as a marker for dihydrotestosterone which is not UV active) were cut out, placed in scintillation cocktail and counted. Finasteride (MK906 or Proscar) was used as the positive control inhibitor. The level of conversion in the negative control was consistent at about 10-15%.

5-alpha-reductase Activity

| Agent | *50% Inhibition |
|---|---|
| #9 Protogracillin | 0 |
| #1 Glabrene | 5 µg/ml |
| #4 Glabridin | 29 µg/ml |
| #5 Licochalcone A | 7 µg/ml |
| #6 Leucoanthocyanidin | 30 µg/ml |
| Crataegus Extract | 31 |
| Serrenoa Extract Saw Palmetto | 11 µg/ml |
| Finasteride Proscar Control | 0.07 µg/ml |

Solutions: The compounds claimed as 5ARIs (glabrene, glabridin; licochalcone A, leucoanthocyanidin and alpha-terpineol) show significant 5ARI activity, with low or no estrogenicity. Compounds with 5ARI and mild estrogenic effect are useful in females.

Protogracillin: The saponin furostanol protogracillin is shown to be a testosterone analog. Protogracillin is often misconstrued to increase testosterone levels; rather it possesses androgenic effect on its own and does not interfere with normal testosterone binding to receptor. Protogracillin serves an anabolic function via a strong androgen receptor affinity testosterone agonist activity. In the case of protogracillin, its receptor affinity is ¹⁄₂₀₀th that of cyproterone's binding affinity, but its effect is anabolic, not antagonistic. Protogracillin also does not interfere with natural testosterone binding, without affecting natural testosterone nor increasing levels of DHT. Testosterone metabolites are mainly DHT, free testosterone and estrogen. If testosterone levels are increased so too are levels of deleterious DHT. This is important in those person predisposed to Testosterone/DHT sensitivities—DHT being a metabolite of testosterone—such as BPH, urinary obstruction, prostate cancer patients, acne, PCOS, hirsuitism, male/female pattern alopecia, hindradenitis ativa, male-impaired urine-flow, males and females who suffer from alopecia, low libido, orgasmic/ejaculatory problems but who should not be exposed to testosterone. Aromatase converts testosterone into estradiol. There is a need for testosterone agonists which are not testosterone and do not raise testosterone and consequential DHT, to achieve metabolic enhancement, ergogenic effect, anabolism, catabolism, muscle enlargement and other anabolic effects. In females with low libido at the perimenopause or menopause, an androgen receptor agonist that is not testosterone nor can be converted into DHT is of use; DHT in women is associated with pattern hair loss and acne and androgenic changes such as vocal cord thickening. Protogracillin's own androgenicity is useful for the method of treatment of low androgenicity and particularly in combination with 5ARIs which may produce unwanted antiandrogenic effects while treating 5ARI-associated conditions.

Furostanolic saponins are glycosylated with one or two sugars (typically pentose or hexose); they are steroidal-alkaloid sapogenin moiety triterpenoids with amphipathic emulsifier properties. The oral toxicity of saponins is very low, but toxicity with IM or IV injection is high due to hemolysis. The major sources of furostanolic saponins are *Tribulus terrestris, Dioscorea deltoidea, Dioscorea collettii, Dioscorea septemloba, Quillaia* bark, *Fenugreek, Castanea sativa, Saponaria officinalis, Paris polyphylla, Dioscorea zingiberensis, Dioscorea pseudojaponica, Yucca, Licorice, Primula* root and *Senega* root. Commercially available furostanolic saponin extracts are available. *Tribulus* contains about 27 different saponins of varying activities, of which 5 are furostanols. Synthesis of saponins is not economically feasible. Ullman's Encyclopedia of Industrial Chemistry details general means of saponin extraction such as from soybeans which contain up to 4% by weight saponins. (Ullman's Encyclopedia of Industrial Chemistry (1993), Vol. A23, pp. 485-498) (US patent applications no 20040013791, 20040101579, 20050123662 and 20050037099) Prior art on extraction of furastanolic saponins focuses on rich sources such as *Tribulus terrestris, Dioscoreas deltoidea* and *Fenugreek* seeds (protodioscin) at neutral pH. (US Patent 20100160616 Novel Process for the Extraction of furastanolic Saponins from *Fenugreek* Seeds)

Prior art discloses furastanolic saponin fractions rich in protodioscin "enhance testosterone production and (are) not for treatment of menopausal symptoms or cancer." (Kumar, 2010) There is very little evidence that any of the furastonolic saponins are testosterone stimulants. One theory often quoted is an assumption that since LH precursors stimulate testosterone, that this must be the cause of reported androgenic effects. The assay results in the present invention show that protogracillin possesses direct androgenomimetic effects. To produce the protogracillin aglycone with higher activity, the present invention claims the method of glycosylated steroidal saponin fraction treated with sugar enzymes, such as in live *Saccharomyces* yeast broth, yeast extract or yeast enzymes in at least a 1:0.0001 ratio for up to 72 hours at approximately 60-70 degrees Fahrenheit to remove sugars from the steroidal moiety.

*Tribulus* contains hundreds of phytochemicals, one of which is protogracillin glycone. The herb has been historically used in Chinese and Indian Ayurvedic medicine and in Europe as a general tonic "energy metabolism" aphrodisiac in men and women. (Dikova, 1983) (Toshkov, 1985) 85% of 212 men experienced increased libido after 30 days and 94% after 60 days. *Tribulus terrestris* contains other steroidal saponins which may have progesterone or estrogenic effects. *Tribulus terrestris*, has long been used in Europe for hormone insufficiency in men and women and for treatment of liver, kidney and urinary tract disease. *Tribulus* may increase ejaculate, sperm count and motility and viability. (Protich, 1983) (Jayaram, 1993) *Tribulus* increased ram rutting behavior and boar sexual reflexes. (Zarkova, 1982) Women with nonovular menstrual cycles given *Tribulus* 750-1500 mg/day on days 5-14 of menstrual cycles showed normalized ovulation in 67% with enhanced rates of pregnancy. In menopausal women, *Tribulus* maintenance doses of 500-750 mg/day showed reduced hot flashes, depression, anxiety, insomnia, ECG changes, chest pressure, sweating and arterial pressure changes with increased libido without increases in FSH, LH, prolactin, estradiol, progesterone and testosterone. (Zarkova, 1982) *Tribulus* had low toxicity in rats and did not induce tumors. (Gendzhev, 1985) *Tribulus* extract appeared to possess aphrodisiac activity. *Tribulus* did not enhance body composition or exercise performance in resistance-trained males which may indicate competing steroidal effects of its steroidal saponins. (Gauthaman, 2008) *Tribulus terrestris* (along with L-arginine, apigenin, *Ginkgo, Turnera diffusa* and *Cinnamon cassia*) have been patented in various combinations as "useful in the treatment of male and female sexual dysfunction impotence, erectile dysfunction, libido disorders, frigidity and anorgasmia without affecting androgen/oestrogen balance, which govern major physiological events in men and women such as the andropause and the menopause. (Gauthaman, 2008).

Saponin extracts of the prior art are intended for a variety of physiological activities such as anti-obesity, immunostimulant activity, anti-ulcer and anti-obesity effect attributed to furastanolic saponins (especially protodioscin) with dosages intended for promoting anabolism. *Tribulus terrestris, Dioscoreas deltoidea, Avena sativa* and *Fenugreek* which contain protogracillin are valued for treating sexual impotency, boosting muscle growth, enhancing testosterone, enhancing LH release, increasing libido, increasing insulin release, improving blood sugar levels, circulation, reducing bad cholesterol, increasing T-cell immunity and antibodies, antiviral and anti-inflammatory effects, and increasing appetite. (United States Patents 20050163874 and 20050208158) Steroidal saponins from the rhizomes of *Dioscorea collettii* var. hypoglauca (Dioscoreaceae), methyl protoneogracillin (NSC-698793) and gracillin (NSC-698787) were cytotoxic against human cancer cell lines from leukemia and eight solid tumor diseases.

Certain supplements are believed to possess androgenic activity. These including androstenedione, boron, octacosanol, *fenugreek, Tribulus terrestri,s* escins, perennisosides, dioscin, gracillin, etc., and the various extracts of the plants like *Nelumbo nucifera, Panax japonicas, Cichorium intybus, Cyperus rotundus, Paeonia suffruticosa*, etc. and *icariin*. (Vasudeva, 2012) There are conflicting reports as to the androgenicity of the whole *Tribulus* extract. In Wistar rats, *Tribulus terrestris* did not stimulate endocrine sensitive tissue such as circulating androgens, sperm production, prostate, seminal vesicle, uterus and vagina, indicating lack of androgenic and estrogenic activity in vivo. (Martino-Andrade, 2009) Also in castrated Wistar rats, a product called Fenu-FG did not change testosterone levels nor affect architecture of testes; the product showed anabolic activity without androgenic activity. Twenty-two Australian elite male rugby league players were given *Tribulus terrestris* 450 mg/day or placebo×5 weeks with muscle training, in a double blind manner. *Tribulus terrestris* did not produce gains in strength or lean muscle mass within 5-28 days, nor did it alter the T/E ratio (testosterone/epitestosterone) and would not risk a positive test based on World Anti-Doping Agency's urinary T/E ratio limit of 4:1. (Rogerson, 2007) In two human females, any testosterone glucuronide or precursor or testosterone was not seen in GC/C/IRMS (gas chromatography/combustion/isotope-ratio-mass-spectrometry) urine sample tests. In 2 females taking 500 mg of *Tribulus terrestris* three times a day for two consecutive days, no impact by *Tribulus terrestris* on endogenous testosterone metabolism was seen in the two subjects. (Saudan, 2008) Conversely, organic (chloroformic and ethanolic fractions) *Tribulus terrestris* extracts in rats were said to have significantly increased levels of free serum testosterone compared to control. (El-Tantawy, 2007) *Tribulus terrestris* was tested in primates, rabbit and rats, administered IV as a bolus dose in an acute study and orally for a chronic study. In primates, testosterone was reportedly increased 52%, DHT 31% and DHEAS (dehydroepiandrosterone sulfate) 29% at 7.5 mg/kg. In rabbits DHT increased statistically significantly over control at 5 and 10 mg/kg. In castrated rats, T levels increased by 25% due to *Tribulus terrestris*. (Gauthaman, 2008) In Sprague-Dawley castrated rats, TT and testosterone increased prostate weight and intracavernous pressure statistically significantly, with improved sexual behavior parameters. (Gauthaman, 2002)

Long term *Tribulus terrestris* use in studies shows no significant adverse or toxic effects. *Tribulus terrestris* may cause gynaecomastia in men, or excess body hair with loss of head hair; this may indicate that other steroidal saponins possess progesterone or estrogenic effects. *Tribulus terrestris* should not be taken by breast or prostate cancer patients, patients with ulcers, stomach inflammation, serious digestion or liver disorders, pregnant women and children, patients with psychosis, schizophrenia, or phaeochromocytoma. *Tribulus terrestris* may have anticoagulation activity and inhibit platelet aggregation, suggesting that TSS from *Dioscorea zingiberensis* may reduce cardiovascular disease risk by anti-thrombotic action. Gracillin and dioscin were synthesized via a novel approach. (Zou, 2003)

Licorice Compounds: Licochalcone A, glabrene and glabridin are potent dihydrotestosterone reductase inhibitors. Licochalcone-A has estrogenic activity. Glabridin is the main isoprenoid-substituted pyranoisoflavan flavonoid of the Spanish and Russian licorice plants. Organic extracts of S and R showed potent antimicrobial and antioxidant activity with glabrene, glabridin, and licochalcones A and B as active principles. (Okada, 1989) Glabridin is a potent antioxidant pyroanoisoflavan flavonoid polyphenol is listed in International Nomenclature of Cosmetic Ingredients (INCI). Glabridin, does not interfere with normal testosterone to androgen receptor binding, and possesses no ERalpha stimulation and reduces estrogenic E2 by 80% at $6\times10^6$ m, while it does help prevent conversion of testosterone into dihydrotestosterone, a potent AR effector which exacerbates many conditions. The pure reference standard of glabridin does not exert any estrogenic response in a concentration range of $1\times10^{-7}$ to $1\times10^{-4}$ M towards both ER subtypes. In concentrations above $1\times10^{-4}$ M, glabridin was toxic to yeast cells. The reference standard of glabridin did not have antagonistic properties towards the ERβ but was shown to be an ERα-selective antagonist. At a concentration of $6\times10^{-6}$ M, glabridin was able to inhibit the E2 response by ~80% without being toxic towards yeast cells. Glabridin displayed ERα-selective antagonism, similar to the ERa-selective antagonist RU 58668. Surprisingly, glabridin did not exert agonistic activity to both ER subtypes. (Simons, 2011) Glabridin demonstrated growth-inhibitory actions on breast cancer cells. (Tamir, 2000) Glabridin is a tyrosinase inhibitor useful against hyperpigmentation and a potent antioxidant and antinflammatory. (Carmelli) (Kwon) Glabridin may be a novel anticancer agent for the treatment of breast cancer in three different ways: inhibition of migration, invasion and angiogenesis. (Hsu) Glabridin demonstrated growth-inhibitory actions on breast cancer cells. (Tamir) Glabridin is yellowish-brown powder, insoluble in water, but soluble in organic solvents such as propylene glycol. Glabrene is a flavonoid classified into isoflav-3-enes. Glabrene only exhibits varying degrees of agonistic responses mainly at on ERa in different tissues but it is a potent 5ARI (IC50=5 ug/ml).

Alpha-Terpineol (AT) is a monoterpenoid alcohol found in *Eupatorium triplinerve* (Asteraceae at 310 ppm), also in *Syzygium aromaticum* (Myrtaceae, common name clove), *Mentha piperita* (Lamiaceae, common name peppermint), also tea tree oil, cajuput oil, pine oil, and petitgrain oil, α-terpineol is one of the two most abundant aroma constituents of lapsang souchong tea (alpha-terpineol originates in the pine smoke used to dry the tea). AT has a pleasant odor similar to lilac and is a common ingredient in perfumes, cosmetics, and flavors. AT is both a natural phytochemical and is commonly manufactured from the readily available alpha-pinene or d-limonene. AT may cause mild irritation to the skin at high doses, and is combustible. AT's other activities include ACE-inhibition, aldose-reductase inhibition, anti-acne activity, anti-inflammation, anti-cariogenic, antiseptic and antibacterial. In the present invention AT is claimed as a 5ARI useful for reduced beard and body hair growth, and against BPH urinary symptoms in men. AT possesses trans-dermal properties meaning it can readily pass through skin. Alpha-terpineol is already claimed as an anti-alopecia agent, without reference to its being a 5ARI.

Leucoanthocyanidin (LAC, flavan-3,4-diols, oligomeric proanthocyanidin, procyanodolic oligomer) is a colorless antioxidant compound related in structure to anthocyanidins and anthocyanidins. Leucoanthocyanidin is found in *Anogeissus latifolia, Crataegus laevigata, Crataegus rhipidophylla, Parthenocissus quinquefolia, Vitus vinefera* (seeds) and *Pinus maritime, Pinus pinaster* pine bark. Leucoanthocyanidin is used for chronic venous insufficiency, arteriosclerosis, retinopathy, diabetes, exercise tolerance, erectile dysfunction, endometriosis, immunostimulation, melasma, Crohn's Disease, MS, psoriasis, RA and SLE. This invention discloses the usefulness of LAC as a mildly estrogenic 5ARI useful for female ARI-responsive disorders at doses of approximately 15-20 mg/day in adults. LAC us is not recommended during pregnancy or lactation.

The following examples of formulations are not delimitors to all possibilities. Dosages and selection of the agents used in accordance with the invention depend on age, weight, clinical condition of the recipient patient, type of radiation or radiocontamination and judgment of practitioner administering therapy. All applications are intended for radioprotection, radiomitigation or radiorecovery. For non-topical administration, oral administration is the preferred route to introduce agents for therapeutic benefit. Preferred dosage forms include powders to be mixed into foods and drinks, powders to be diluted and then mixed into drinks, capsules, wafers, nanoparticles, dragees, syrups, suspensions, elixers, lozenges, pills, troches, sublinguals, buccals, nasal sprays, rectal doses, chewing gum, lollipops, dissolving thin-films, pastilles, gelatins, designer foods, drink mixes, puddings, cereals, juices, smoothies, fizzy-drinks, etc. All topical formulations may be oil-in-water or water-in-oil emulsions, gels, lotions, liquids, creams, pastes, washes, suspensions, lotions, ointments or designed as micelles, nanoparticles, liposomes or microparticles. Excipients in formulations may be inert waxes, polymers, sugars, etc. such as PEG-s, polysorbate-s, waxes, celluloses, fats, and any other accepted excipient. This invention relates to 5 alpha-reductase inhibitor molecules purchased as isolated agents (such as glabridin from Alchem Intemationl Ltd., India). The amount will vary depending on the formulation and the performance desired. Preferably, the whitening agent is present in the amount from 0.0001% to 20%, or extracted from various parts (leaves, pericarps, berries, bark, fruit, roots, and/or pericarps) of a variety of plants using a variety of solvents including water, organic solvents, inorganic solvents, etc. It is not the purpose of this invention to describe the exact organic solvent mechanism by which to extract the active compounds; only that these compounds will be found in certain segments of a variety of plants and that they can be extracted therefrom. The 5-alpha-reductase inhibiting substances will be used as USP purity and formulated into drug products. The preferred embodiments include any dosage form, oral, injection, absorption, patch, food, topical or other which may deliver the active components.

Embodiment #2

A combination 5-alpha-reductase inhibitor plus androgenic analog in capsule form containing 45 mg grape seed leucoanthocyanidin combined with 150 mg protogracillin for low androgenicity and male pattern alopecia symptoms.

Embodiment #3

A lotion containing up to 18% w/v alpha terpineol applied daily to the male face and chest to reduce face and body hair, respectively, or to the prostate region for improved BPH symptoms.

The drawings include that of the molecular structures of: FIG. 1: glabridin, FIG. 2: protogracillin, FIG. 3: leucoanthocyanidin, FIG. 4: glabrene and FIG. 5: alpha-Terpineol.

The invention claimed is:
1. A novel androgen effector method for treating diseases responsive to 5-alpha reductase inhibition and non-antiandrogenicity, comprising administering to a human or mam- mal subject in need thereof a therapeutic composition or formulation comprising a therapeutically effective amount of 5-alpha reductase inhibitor glabridin as an active principle, via an effective dosage form in a pharmaceutically acceptable vehicle, wherein 5-alpha reductase is inhibited and levels of dihydrotestosterone in the subject are reduced, and wherein the overall level of testosterone to androgen receptor signaling in the subject is not reduced in the presence of glabridin;
  wherein the therapy may or may not exert an estrogenic effect;
  said nonestrogenic 5-alpha reductase inhibiting therapeutically effective amount of glabridin being that which achieves a serum concentration of about the IC50 of 29 ug/ml for glabridin, but less than 10-4 M (32 ug/ml) and more than 10-7 M (32 ng/ml) glabridin based on pure reference standard of glabridin;
  said estrogenic 5-alpha reductase inhibiting therapeutically effective amount of glabridin being that which achieves a serum concentration above 10-4 M (32 ug/ml) glabridin based on pure reference standard of glabridin;
  said therapeutic composition of formulation comprises 0.0001 wt%-20 wt% glabridin plus one or more excipients.

2. A method for treating diseases responsive to 5-alpha reductase inhibition and non-antiandrogenicity comprising the steps of administering 0.0001 wt%-20 wt% glabridin as the active principle in a therapeutic composition or formulation to a human or mammal subject in need thereof, wherein the improvement comprises that 5-alpha reductase is inhibited while the overall level of testosterone to androgen receptor signaling in the subject is not reduced in the presence of glabridin and glabridin when dosed to achieve a serum concentration of between 10-7 M and 10-4 M is estrogenic.

3. A novel androgen effector method for treating diseases responsive to 5-alpha reductase inhibition without reducing testosterone to androgen receptor agonism, consisting essentially of administering to a human or mammal subject in need thereof a therapeutic composition or formulation of 0.0001 wt%-20 wt% glabridin delivering a therapeutically effective amount of 5-alpha reductase inhibitor glabridin as the active principle, and furthermore optionally containing at least one further active agent selected from the list consisting of alpha-linolenic acid, alpha terpineol, Angelica Tenuissima, arachidonic acid, artocarpin, beta-sitosterol, biochanin-A, coconut medium chain fatty acids, daidzein, dutasteride, epicatechin, epigallocatechin, finasteride, flutamide, gamma linolenic acid (GLA), genistein, glabrene, leucoanthocyanidin, licochalcone A, linoleic acid, myristoleic acid, oleic acid, palm fruit kernel, palmitic acid, palmitoleic acid, papverine, Perilla sikokiana, PDE5 inhibitors, phentolamine, phenoxybenzamine, phytosterlos, prostaglandin E2, pumpkin seed extract, protogracillin, Pygium africanum, S. Flavescens, secoisolariciresinol, Serenoa Repens, sildenafil, solasodine, stearic acid, testosterone receptor agonists, unsaturated fatty acids, vasoacive intestinal polypeptide or VIP, and other 5-alpha reductase inhibitor agents via an effective dosage form in a pharmaceutically acceptable vehicle, wherein 5-alpha reductase is inhibited and levels of dihydrotestosterone in the subject are reduced.

4. A novel androgen effector method for treating diseases responsive to 5-alpha reductase inhibition, majority non-antiandrogenicity, and to estrogenicity, comprising administering to a human or mammal subject in need thereof a therapeutic composition or formulation comprising a therapeutically effective amount of the 5-alpha reductase inhibitor glabrene or leucoanthocyandin as an active principle, via an effective dosage form in a pharmaceutically acceptable vehicle;
  wherein said treatment thereby maintains majority binding activity for agonism of testosterone to androgen receptor in the presence of glabrene, is estrogenic, and inhibits 5-alpha reductase, and levels of dihydrotestosterone in the subject are reduced;
  said effective amount of active principle is that which achieves a therapeutic serum level of about the IC50 of 5 ug/ml for glabrene and 30 ug/ml for leucoanthocyanidin.

5. A novel androgen effector method for treating diseases responsive to 5-alpha reductase inhibition and majority non-antiandrogenicity and to estrogenicity, consisting essentially of administering to a human or mammal subject in need thereof a therapeutic composition or formulation consisting essentially of a therapeutically effective amount of the 5-alpha reductase inhibitor glabrene or leucoanthocyanidin as an active principle, via an effective dosage form in a pharmaceutically acceptable vehicle, and furthermore optionally containing at least one further active agent selected from the list consisting of alpha-linolenic acid, alpha terpineol, Angelica Tenuissima, arachidonic acid, artocarpin, beta-sitosterol biochanin-A, coconut medium chain fatty acids, daidzein, dutasteride, epicatechin, epigallocatechin, finasteride, flutamide, gamma linoleic acid (GLA), genistein, glabrene, leucoanthocyanidin, licochalcone A, linoleic acid, myristoleic acid, oleic acid, palm fruit kernel, palmitic acid, palmitoleic acid, papverine, Perilla sikokiana, PDE5 inhibitors, phentolamine, phenoxybenzamine, phytosterols, prostaglandin E2, pumpkin seed extract, protogracillin, Pygium africanum, S. Flavescens, secoisolariciresinol, Serenoa Repens, sildenafil, solasodine, stearic acid, testosterone, testosterone receptor agonists, unsaturated fatty acids, vasoactive intestinal polypeptide or VIP, and other 5-alpha reductase inhibitor agents, wherein said treatment thereby maintains majority binding activity for agonism of testosterone to androgen receptor in the presence of leucoanthocyanidin or glabrene, is estrogenic, and inhibits 5-alpha reductase and levels of dihydrotestosterone in the subject are reduced.

6. The method of claim 3 or 5 whereby the composition contains a therapeutically effective amount of at least one further agent selected from the list consisting of alpha-linolenic acid, alpha terpineol, Angelica Tenuissima, arachidonic acid, artocarpin, beta-sitosterol, biochanin-A, coconut medium chain fatty acids, daidzein, dutasteride, epicatechin, epigallocatechin, finasteride, flutamide, gamma linolenic acid (GLA), genistein, glabrene, leucoanthocyanidin, licochalcone A, linoleic acid, myristoleic acid, oleic acid, palm fruit kernel, palmitic acid, palmitoleic acid, papaverine, Perilla sikokiana, PDE5 inhibitors, phentolamine, phenoxybenzamine, phytosterols, prostaglandin E2, pumpkin seed extract, protogracillian, Pygium africanum, S. Flavescens, secoisolariciresinol, Serenoa Repens, sildenafil, solasodine, stearic acid, testosterone, testosterone receptor agonists, unsaturated fatty acids, vasoactive intestinal polypeptide or VIP, and other 5-alpha reductase inhibitor agents.

7. The method of claim 5 wherein the 5-alpha reductase inhibitor is leucoanthocyanidin, and said leucoanthocyanidin is administered in a dose of 10-20 mg/day.

* * * * *